United States Patent [19]
Ghisalba et al.

[11] Patent Number: 6,147,211
[45] Date of Patent: Nov. 14, 2000

[54] METHOD FOR TREATING CYCLIC PHOSPHATE COMPOUND

[75] Inventors: Oreste Ghisalba, Reinach; Guy Joel Christian Marais, Olten; Pierre Martin, Rheinfelden, all of Switzerland

[73] Assignee: Novartis AG, Basel, Switzerland

[21] Appl. No.: 09/167,191

[22] Filed: Oct. 6, 1998

[51] Int. Cl.$^7$ .................. C07F 9/6512; C07F 9/6521; C12N 15/31; C12N 9/16
[52] U.S. Cl. ................. 544/244; 544/243; 435/89; 435/92
[58] Field of Search .................. 544/243, 244; 435/89, 92

[56] References Cited

U.S. PATENT DOCUMENTS 5,382,519  1/1995  Dunlap et al. .................. 435/69.1

FOREIGN PATENT DOCUMENTS

WO 94/16063  7/1994  WIPO.

OTHER PUBLICATIONS

Tazawa et al., Biochemistry, vol. 11, No. 26, 1972 pp. 4931–36.
Altman et al., Chimia 50, No. 4, pp. 168–176 Apr. 1996.
Callahan et al., The Journal of Biological Chemistry, vol. 270, No. 29, pp. 17627–17632, Jul. 21, 1995.
Dunlap et al., Journal of General Microbiology, vol. 138, pp. 115–123 (1992).
Dunlap et al., Journal of Bacteriology, vol. 175, No. 15, pp. 4615–4624, Aug. 1993.
Martin, P., Separatum Helvetica Chimica Acta, vol. 78, pp. 486–504 (1995).
Martin, P., Separatum Helvetica Chimica Acta, vol. 79, pp. 1930–1938, (1996).
Mesmaeker et al., Accounts of Chemical Research, vol. 28, No. 9, pp. 366–374.
Tazawa et al., Biochemistry, vol. 11, No. 26, pp. 4931 to 4937 (1972).

*Primary Examiner*—Mukund J. Shah
*Assistant Examiner*—Pavanaram K Sripada
*Attorney, Agent, or Firm*—Michael U. Lee; Myra H. McCormack

[57] ABSTRACT

The invention relates to a compound of formula (I)

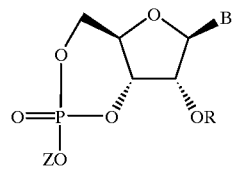

Formula (I)

Wherein:
B is adenine, guanine or hypoxanthine
Z is hydrogen or a negative charge
R is —$[CH_2CH(R^1)-O]_n$-$R^2$, —$CH_2CH_2X$, in which $R^1$ is hydrogen or ($C_{1-6}$) alkyl $R^2$ is hydrogen or ($C_{1-6}$) alkyl n is a number from 1 to 6

X is OH, F, $NR^3R^4$ $R^3$ and $R^4$ are independently from each other hydrogen or ($C_{1-6}$) alkyl and to methods of enzymatically treating these compounds with biocatalysts having cyclic phosphodiesterase activity.

12 Claims, No Drawings

METHOD FOR TREATING CYCLIC PHOSPHATE COMPOUND

Antisense therapy requires the use of modified nucleotides in order to block gene expression by preventing messenger RNA (mRNA) translation into active proteins. The criteria requested for optimal activity of an antisense oligonucleotide are resistance to endo- and exonucleases, affinity and specificity for the targeted mRNA sequence as well as easy uptake by the concerned cells, and finally destruction or inactivation of the mRNA. Certain chemical modifications of the nucleotides or of the phosphate backbone can allow such biological activity and several approaches have been used to this end.

The first-generation antisense oligonucleotides consist of DNA in which a sulfur atom has been incorporated in replacement of an equatorial oxygen atom in the phosphate backbone. This PS backbone confers a better resistance to nucleases, although it lowers the affinity of the oligonucleotide for its target. The mechanism of action involves RNase H, an enzyme that specifically degrades the RNA in a DNA:RNA complex, therefore destroying the mRNA. The second-generation strategies use mixtures of modified oligoribonucleotides and oligodeoxyribonucleotides in chimeric molecules. The part of the molecule composed of ribonucleotides is then responsible for the affinity for the targeted sequence, whereas the part containing the deoxyribonucleotides acts as a substrate for RNase H which cleaves the targeted mRNA. The ribonucleotides are modified at the C2' position of the sugar where different substituents can be attached.

Chemical synthesis of the 2'-modified nucleotides is currently very expensive and, as the demand for such compound is expected to soar in the near future, their biosynthesis by an appropriate microorganism would markedly lower the cost of their production, especially if it is possible to start with cheap compounds available in large amounts.

Cyclic nucleotides are essential elements in many biochemical processes of the eukaryotic and prokaryotic cell cycles, particularly adenosine 3',5' cyclic monophosphate and guanosine 3',5' cyclic monophosphate. These compounds constitute the most adequate starting material for the purpose of the present invention.

It is known that such natural cyclic nucleotides could be transformed to their corresponding 5'-nucleoside monophosphates by 3',5'-cyclic nucleotide phosphodiesterases e.g., from *Vibrio fischeri* (WO 94116063, Journal of Bacteriology, Vol. 175, No. 15, p. 4615–4624). Furthermore the conversion of 2' O-methyl- and 2' O-ethyl- nucleoside 3',5'-cyclic phosphates to the corresponding 5'-phosphates by enzymatic hydrolysis has been published (Biochemistry, Vol. 11, No. 26, 1972, p. 4931–4937).

There is still a need for a process which allows the synthesis of nucleotides with more complex 2'-substituents. Surprisingly an enzymatic process has now been found to produce nucleosides with such more complex 2'-substituents.

The invention relates to a process comprising treatment of compounds of Formula (I)

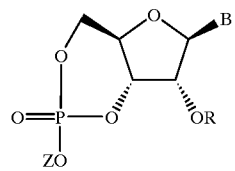

Formula (I)

wherein
B is adenine, guanine or hypoxanthine
Z is hydrogen or a negative charge
R is $-[CH_2CH(R^1)-O]_n-R^2$, $-CH_2CH_2X$, in which
  $R^1$ is hydrogen or $(C_1-C_6)$ alkyl
  $R^2$ is hydrogen or $(C_1-C_6)$ alkyl
  n is a number from 1 to 6
  X is OH, F, $NR^3R^4$
  $R^3$ and $R^4$ are independently from each other hydrogen or $(C_1-C_6)$ alkyl with a biocatalyst having cyclic phosphodiesterase activity.

The product of such process may in a second step be hydrolysed to a compound of Formula (II).

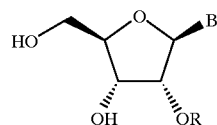

Formula (II)

wherein B and R have the same meaning as defined above. This hydrolysis could be done chemically or enzymatically. Biocatalyst having cyclic phosphodiesterase activity may be for the purpose of this invention a purified enzyme, from original or recombinant source, a partially purified enzyme, a crude cell extract, enzymes immobilized or caught in partially broken cells or cell debris. The biocatalyst may be used in solution, suspension or in immobilized form (matrix bound) according to routine processes, e.g. batch or continuous, known in the art. Source for the biocatalyst may be every organism, e.g. animal organs, microorganisms like fungi or bacteria, which comprise an enzyme suitable for being used as biocatalyst in the above process. Whether a microorganism contains such enzyme can easily be evaluated by a test which comprises the comparative growth of an organism on a medium containing only salts and Tris buffer (minimal medium, described in Dunlap et al. J. Gen. Microbiol. 1992, 138, 115–123) and in parallel on the same medium supplemented with 1 to 5 mM of compound of formula (I). Any microorganism containing an extracellular or periplasmic (for gram-negative bacteria) enzyme able to hydrolyse the substrate will grow on the supplemented medium. The minimal medium serves as a negative control differentiating between microorganisms able to grow on Tris or on cAMP only, as some microbes are known to be able to utilise Tris as a nutrient.

For microorganism possessing a cytoplasmic phophodiesterase (as it is the case for many bacteria, e.g., *Escherichia coli* or *Salmonella typhimurium*), growth on nutrient agar is necessary. The cell disruption supernatant has to be assayed as the cytoplasmic membrane is known to be fairly impermeable to cyclic nucleotides.

Accordingly the present invention also comprises new enzymes which can be identified in the above tests.

A preferred embodiment of the invention is the use of the gram negative bacterium *Serratia marcescens,* particularly the use of strain DSM 30121 as the source of biocatalyst having cyclic nucleotide phophodiesterase activity. Such biocatalyst having cyclic nucleotide phosphodiesterase activity is used as a purified enzyme, a partially purified enzyme or as a crude cell extract.

For the specific cleavage of the 3',5' nucleoside cyclic monophosphate to the 5'-monophosphate only the enzymatic cleavage is selective and therefore clearly superior to chemical hydrolysis.

Furthermore the invention relates to compounds of formula (I)

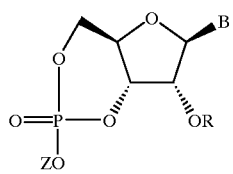

Formula (I)

wherein
B is adenine, guanine or hypoxanthine
Z is hydrogen or a negative charge
R is —[$CH_2CH(R^1)$—O]$_n$-$R^2$, —$CH_2CH_2X$, in which
$R^1$ is hydrogen or ($C_1$–$C_6$) alkyl
$R^2$ is hydrogen or ($C_1$–$C_6$) alkyl
n is a number from 1 to 6
X is OH, F, $NR^3R^4$
$R^3$ and $R^4$ are independently from each other hydrogen or ($C_1$–$C_6$) alkyl Preferred are compounds of formula (I) wherein R is $CH_2CH_2OR^2$, preferably $CH_2CH_2OCH_3$ further preferred are compounds wherein B is adenine.

The compounds of formula (I) could be synthesized by reacting the corresponding nucleoside 3',5' cyclic monophosphates with an alkylation reagent, for example R-halogene, especially R-Br or R-I.

Furthermore the invention comprises the use of a biocatalyst having cyclic phosphodiesterase activity for the preparation of compounds of formula (II).

The following examples shall illustrate the invention but not restrict it.

EXAMPLES

Compounds

Example 1

Preparation of 2'—O(2-Methoxyethyl)-adenosine 3',5'-cyclic-phosphate (2'MOE cAMP)

5.0 g (15.2 mmol) adenosine-3':5'-cyclic phosphate are dissolved in 60 ml DMSO. 1.28 g(22.8 mmol) powdered KOH and 1.80 ml (20 mmol) 2-chloroethylmethylether are added. The mixture is stirred for 30 h at 70° C., after 21 h additional 0.64 g KOH and 0.9 ml 2-chloroethylmethylether are added. After cooling the mixture is evaporated and the residue is purified by chromatography ($SiO_2$, $CH_2Cl_2$/MeOH/$H_2O$ 60:30:4). Obtained are beige crystals, Mp>250° C.

$^{31}$P-NMR ($D_2O$): −0.759 ppm MS: 386(M-H)$^-$

Example 2

Preparation of Sodium 2'-O(2-Methoxyethyl)-guanosine-3',5'-cyclic monophosphate (2'MOE cGMP)

0.40 g (1.09 mmol) sodium guanosine-3':5'-cyclic monophosphate are dissolved in 4 ml DMSO. 0.73 g powdered KOH and 0.18 g (1.31 mmol) 2-bromoethylmethylether are added. The mixture is stirred for 30 h at 70° C. After cooling the mixture is evaporated and the residue is purified by chromatography ($SiO_2$, $CH_2Cl_2$/MeOH/$H_2O$ 60:30:4). Obtained are colourless crystals, $^{31}$P-NMR ($D_2O$): −3.59 ppm MS: 402(M-Na)$^-$ The substrates used for enzyme activity assays are dissolved in phosphate buffer pH 7.0 to the required concentration.

Fermentation conditions

*Serratia marcescens* strain DSM 30121 is grown for 48 hrs in Petri dishes containing Luria-Bertani [LB] Agar (1% Tryptone [Merck 07213]; 0.5% Yeast Extract [Fluka 70161]; 86 mM NaCl [Fluka 71382]; 50 mM Tris-HCl, pH 7.5 [Merck 8382]; 1.5% Bacto-Agar [Difco 0140-01]) at 30° C. (Memmert Incubator, Haska AG, Bern, Switzerland). One single colony is subsequently used to inoculate 25 ml of LB Broth contained in a 100-ml shake-flask. This culture is then incubated at 30° C. and shaken at 200 rpm (Infors HT Shaker, Infors AG, Bottmingen, Switzerland) for another 48 hrs.

Activity assay

After incubation, the whole volume of the culture is centrifuged at 9 000 rpm for 20 minutes at ca. 4° C. (DuPont Instruments Sorvall® RC-5B Refrigerated Superspeed Centrifuge, Digitana AG, Horgen, Switzerland; rotor SS-34).

The supernatant (fraction A) is recuperated and 360 μl are placed in an Eppendorf tube. Fourty μl of a 100 mM solution of substrate are then added to the reaction mixture and incubated overnight at 30° C.

The pellet is resuspended in 1 ml of distilled water and 40 μl of this whole-cell suspension (fraction B) are placed in an Eppendorf tube to which 360 μl of a 10 mM solution of the substrate are added. The incubation conditions are the same as for the supernatant fraction.

Six hundred μl of the resuspended 9 000 rpm pellet are placed in an Eppendorf tube containing 1.2 g of glass beads (Roth AG, Karlsruhe, Germany). The cells are subsequently broken in a mechanical cell disruptor (Retsch Mill, Schieritz & Hauenstein AG, Arlesheim, Switzerland) set at 100% for 10 minutes. The mixture is then centrifugated at 14 000 rpm (Bench Centrifuge Biofuge 15, Heraeus AG, Zürich, Switzerland) and 40 μl of the supernatant (fraction C) is placed in an Eppendorf tube with 360 μl of a 10 mM solution of the substrate. Incubation is realised in the same manner as preceedingly.

After incubation, the three different fractions (fraction A:supernatant, fraction B: whole-cell suspension and fraction C: disrupted cells supernatant) are treated the same way. The reaction is stopped by the addition of 400 μl of methanol (Fluka 65543). After 5 minutes of extraction at room temperature, the tubes are centrifugated at 14 000 rpm for 5 minutes (Bench Centrifuge Biofuge 15) and the supernatant transfered to HPLC tubes for analysis.

Blanks are made with the substrate solution being replaced by an equivalent volume of phosphate buffer pH 7.0.

Determination of activity

The activity is qualitatively determined by observing the appearance of the substrate and product(s) of the activity assay as peaks on a HPLC profile. The detection of peaks is compared to standards containing only one compound (cAMP, 3'-AMP, 5'-AMP, adenosine, and their 2'-modified counterparts). A peak showing on the assay's chromatogramme at the same or at a very close retention time as that of a standard, and moreover absent from the blank, is considered to be the same compound as the standard with a minimum risk of error.

The chromatographic system used for the detection of nucleotides in the activity assays is composed of the following elements (all from Merck-Hitachi): AS-2000 autosampler, L-6210 pump (flow rate=0.8 ml.min$^{-1}$), L-4000 UV-vis detector (detection wavelength set at 254 nm) and D-2500 integrator. The column is a Merck Lichrocart® 125-4 packed with Lichrospher® 100 RP-18 (5 μm). A precolumn Merck Lichrocart® 4-4 is also used upstream from the column.

The solvent system is composed of 10 mm phosphate buffer, pH 4.0 (solvent A) and Methanol (solvent B) and two different gradients are applied depending on whether natural or modified nucleotides are used for the assay:

| Time (min) | % A | % B |
|---|---|---|
| Gradient for natural nucleotides: | | |
| 0.0 | 95 | 5 |
| 9.0 | 95 | 5 |
| 15.0 | 80 | 20 |
| 17.0 | 0 | 100 |
| 19.0 | 0 | 100 |
| 19.5 | 95 | 5 |
| 25.0 | 95 | 5 |
| Gradient for modified nucleotides: | | |
| 0.0 | 95 | 5 |
| 12.0 | 85 | 15 |
| 19.0 | 40 | 60 |
| 19.5 | 0 | 100 |
| 26.0 | 0 | 100 |
| 27.0 | 95 | 5 |
| 30.0 | 95 | 5 |

The HPLC profiles obtained for the activity assays are compared with profiles of standards in order to identify the peaks.

Results

Intact cells (fraction B) of *Serratia marcescens* are found to degrade over 99% of added cAMP, whereas 2'MOE cAMP is about 85% degraded, the presence of 2'MOE adenosine was also detected in the assay. Disrupted cells (fraction C) are able to hydrolyse about 99% or more of both cAMP and 2' MOE cAMP. The cell free culture supernatant (fraction A) shows hydrolysis of cAMP and 2'MOE cAMP in proportions of about 97% and about 50% respectively. This fraction is also able to degrade cAMP (ca. 85–89%) and cCMP (ca. 10%).

Chemical cleavage of the 5'-monophosphates 1 ml acetic acid and 3 mg $CeSO_4$ are added to a solution of 7.3 mg of the ammonium salt of 2'-O(2-Methoxyethyl)-adenosine-5'-monophosphate in 30 ml $H_2O$. After 2 days the mixture is evaporated and chromatographed ($SiO_2$, MeOH/AcOH 1:4). 2'O(2-Methoxyethyl)-adenosine is obtained as a white powder.

What is claimed is:

1. A method for enzymatically treating a compound comprising the step of:

treating a compound of Formula (I)

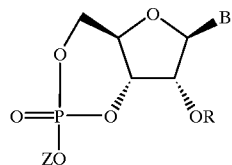

Formula (I)

with a biocatalyst having cyclic phosphodiesterase activity wherein R is —$[CH_2CH(R^1)—O]_n$-$R^2$ or —$CH_2CH_2X$, and wherein $R^1$ is hydrogen or ($C_1$–$C_6$) alkyl, n is a number form 1 to 6, X is OH, F, $NR^3R^4$, and $R^3$ and $R^4$ are independently from each other hydrogen or ($C_1$–$C_6$) alkyl;

B is adenine, guanine or hypoxanthine; and,

Z is hydrogen or a negative charge,

Wherein the source of the biocatalyst having cyclic phosphodiesterase activity is a gram-negative bacterium.

2. The method of claim 1 wherein the source of the biocatalyst having cyclic phosphodiesterase activity is the gram negative bacterium *Serratia marcescens*.

3. The method of claim 1 wherein in formula (I) R is $CH_2CH_2OR^2$.

4. The method of claim 1 wherein B is adenine or hypoxanthine.

5. The method of claim 4 wherein the method further comprises the step of hydrolyzing the product of the reaction of the biocatalyst with a compound of formula (I)

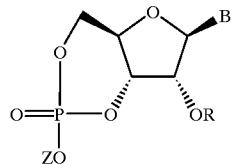

Formula (I)

chemically or enzymatically in a second reaction step to a compound of formula (II)

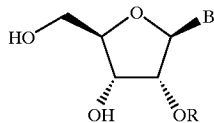

Formula (II)

wherein R is —$[CH_2CH(R^1)—O]_n$-$R^2$, or —$CH_2CH_2X$, and wherein $R^1$ is hydrogen or ($C_1$–$C_6$) alkyl, $R_2$ is hydrogen or ($C_1$–$C_6$) alkyl, n is a number from 1 to 6, X is OH, F, $NR^3R^4$, and $R^3$ and $R^4$ are independently from each other hydrogen or ($C_1$–$C_6$) alkyl and B is adenine, guanine or hypoxanthine.

6. The method of claim 2 wherein the bacterium is *Serratia marcescens* strain DSM 30201.

7. The method of claim 3 wherein R is $CH_2CH_2OCH_3$.

8. The method of claim 5 wherein in formula (II) R is $CH_2CH_2OR^2$.

9. The method of claim 8 wherein R is $CH_2CH_2OCH_3$.

10. The method of claim 4 wherein B is adenine.

11. The method of claim 5 where B is adenine or hypoxanthine.

12. A method for preparing a compound comprising the step of:

contacting a biocatalyst having cyclic phosphodiesterase activity with a compound of formula (I)

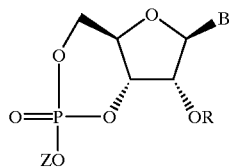

Formula (I)

wherein:
B is adenine, guanine or hypoxanthine;
Z is hydrogen or a negative charge; and
R is —[CH$_2$CH(R$^1$)—O]$_n$-R$^2$ or —CH$_2$CH$_2$X, wherein R$^1$ is hydrogen or (C$_1$–C$_6$) alkyl,
R$_2$ is hydrogen or (C$_1$–C$_6$) alkyl,
n is a number from 1 to 6,
X is OH, F, NR$^3$R$^4$, and
R$^3$ and R$^4$ are independently from each other hydrogen or (C$_1$–C$_6$) alkyl to produce a compound of formula (II)

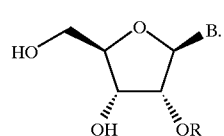

Formula (II)

* * * * *

UNITED STATES PATENT AND TRADEMARK OFFICE
CERTIFICATE OF CORRECTION

PATENT NO.    : 6,147,211
DATED         : November 14, 2000
INVENTOR(S)   : Ghisalba et al.

It is certified that error appears in the above-identified patent and that said Letters Patent is hereby corrected as shown below:

Column 6,
Line 27, "claim 4" should read -- claim 1 --.

Signed and Sealed this

Tenth Day of May, 2005

JON W. DUDAS
*Director of the United States Patent and Trademark Office*